United States Patent
Hall et al.

(10) Patent No.: US 10,408,849 B2
(45) Date of Patent: *Sep. 10, 2019

(54) METHOD OF DETERMINING CONSUMPTION OF DECAYED DRUG THROUGH DRUG TAGGANTS

(71) Applicants: David R. Hall, Provo, UT (US); Dan Allen, Springville, UT (US); Conrad Rosenbrock, Provo, UT (US); Daniel Hendricks, Provo, UT (US); Andrew Nguyen, Provo, UT (US); Steven J. M. Butala, Provo, UT (US); Travis Niederhauser, Mapleton, UT (US); Terrece Pearman, Draper, UT (US); Joe Fox, Spanish Fork, UT (US)

(72) Inventors: David R. Hall, Provo, UT (US); Dan Allen, Springville, UT (US); Conrad Rosenbrock, Provo, UT (US); Daniel Hendricks, Provo, UT (US); Andrew Nguyen, Provo, UT (US); Steven J. M. Butala, Provo, UT (US); Travis Niederhauser, Mapleton, UT (US); Terrece Pearman, Draper, UT (US); Joe Fox, Spanish Fork, UT (US)

(*) Notice: Subject to any disclaimer, the term of this patent is extended or adjusted under 35 U.S.C. 154(b) by 90 days.

This patent is subject to a terminal disclaimer.

(21) Appl. No.: 15/494,089

(22) Filed: Apr. 21, 2017

(65) Prior Publication Data
US 2018/0306825 A1    Oct. 25, 2018

(51) Int. Cl.
| | | |
|---|---|---|
| G01N 33/94 | (2006.01) | |
| G01N 33/493 | (2006.01) | |
| G01N 33/58 | (2006.01) | |
| G01N 33/15 | (2006.01) | |
| G01N 21/88 | (2006.01) | |
| A61B 10/00 | (2006.01) | |
| A61B 5/15 | (2006.01) | |

(52) U.S. Cl.
CPC ............... *G01N 33/94* (2013.01); *A61B 5/15* (2013.01); *A61B 10/007* (2013.01); *A61B 10/0038* (2013.01); *A61B 10/0051* (2013.01); *G01N 21/8803* (2013.01); *G01N 33/15* (2013.01); *G01N 33/493* (2013.01); *G01N 33/58* (2013.01); *A61B 2010/0061* (2013.01); *A61B 2010/0077* (2013.01)

(58) Field of Classification Search
None
See application file for complete search history.

(56) References Cited

U.S. PATENT DOCUMENTS

| | | | | |
|---|---|---|---|---|
| 6,025,200 A | * | 2/2000 | Kaish | G01N 21/643 422/83 |
| 2014/0065171 A1 | * | 3/2014 | Geierstanger | C07K 16/00 424/179.1 |

OTHER PUBLICATIONS

Isin, E.M. et al. 2012. Use of radiolabeled compounds in drug metabolism and pharmacokinetic studies. Chemical Research in Toxicology 25: 532-542. specif. pp. 532, 536, 537, 538.*
Lee, Y.-H. et al. 2015. Reduction of oxygen inhibition effect for microalgal growth using fluoroalkylated methoxy polyethylene glycol-stabilized perfluorocarbon nano-oxygen carriers. Process Biochemistry 50: 1119-1127. specif. pp. 1119.*
Henning, T. 2002. Polyethylene glycols (PEGs) and the pharmaceutical industry. Clariant GmbH. Pharma. Chem., pp. 57-59. specif. pp. 57, 58, 59.*
Sheraz, M.A. et al. 2014. Photo, thermal and chemical degradation of riboflavin. Beilstein Journal of Organic Chemistry 10: 1999-2012. specif. pp. 1999, 2000, 2001, 2002, 2004, 2008, 2009.*
Saenz, A. 2009. Smart toilets: doctors in your bathroom. Datasheet [online]. Singularity Education Group. [retrieved on May 7, 2018]. Retrieved from the internet: <https://singularityhub.com/2009/05/12/smart-toilets-doctors-in-your-bathroorn/#m.0001y4o5itr122uesaygr8rrwc5kyf> pp. 1-3. specif. pp. 1, 2, 3.*

* cited by examiner

*Primary Examiner* — Renee Claytor
*Assistant Examiner* — Sharon M. Papciak (57) ABSTRACT

We disclose a method of using taggants to assess how and to what extent a drug in a drug composition that a user has consumed has decayed in response to storage conditions and time. The taggants may decay in response to environmental conditions which cause different drugs to lose their efficacy. These environmental conditions may include light, temperature, oxidation, and age. The taggants may be detected in biological samples, including urine and feces. By identifying the taggants, the drug composition and other information relating to the drug may be identified. Additionally, quantification of the different taggants may be used to determine whether the drug in the drug composition has been exposed to environmental conditions which may reduce its efficacy.

17 Claims, 7 Drawing Sheets

| Name | Structure |
|---|---|
| Polyethylene Glycol |  |
| Ethylene Vinyl Acetate |  |
| Povidone |  |
| Copovidone |  |
| Propylparaben |  |
| Methylparaben |  |
| Sucralose |  |

FIG. 4

| Name | Structure |
|---|---|
| Steviol Glycoside |  |
| Riboflavin |  |
| Oleic Acid |  |
| Tartaric Acid |  |
| 1, 8-eucalyptol |  |
| Trans-anethole |  |
| Limonene-2D |  |

| NAME | AVG MW (g/mol) | Example MW Range (g/mol) |
|---|---|---|
| PEG 400 | 400 | 380-420 |
| PEG 800 | 800 | 720-880 |
| PEG 1000 | 1000 | 950-1050 |
| PEG 1500 | 1500 | 1300-1650 |
| PEG 2000 | 2000 | 1900-2200 |

FIG. 7

METHOD OF DETERMINING CONSUMPTION OF DECAYED DRUG THROUGH DRUG TAGGANTS

BACKGROUND

Field of the Invention

This disclosure relates to methods of tracking and identifying the age or amount of degradation of pharmaceuticals after consumption using drug tags.

Background of the Invention

Consumption of drugs which have reduced efficacy or are unsafe due to aging or prolonged exposure to certain conditions creates a health risk. Methods for managing this problem include printing an expiration date on the drug packaging and applying aging strips that change color over time to drug packaging. However, these methods simply predict the status of a consumed drug but do not actually detect the consumption of outdated or degraded drug.

An additional problem is abuse of prescription drugs. If a patient does not consume all the prescribed medication a person other than the patient may consume that medication. This may occur when the patient shares unused drug with another or illegally sells the drug. The drug may not be effective when the other person receives it due to improper storage.

In these and other scenarios it is beneficial to not only be able to identify the consumed drug, and whether the drug has experienced significant degradation from age, extreme temperature, light, or other environmental conditions.

A method is need to tag drug compositions in a way that both identifies the drug composition and determines whether it has aged or decomposed by analyzing a biological sample collected from a user who has consumed the tagged drug composition.

BRIEF SUMMARY OF THE INVENTION

We disclose a method of using one or more taggants which may be added to drug compositions to assess decay of the drug in the drug composition due to environment or age. The taggants may be detectable in a biological sample, including urine or feces. The taggants may have one or more decay characteristics which may include light sensitivity, temperature sensitivity, and decay due to chemical degradation over time. The drug composition may include taggants that possess the same decay characteristics as the drug in the drug composition. The drug composition may also include taggants that possess different decay characteristics relative to the drug in the drug composition. Alternatively, multiple taggants, some with the same and some with different decay characteristics may be included.

The taggants may be present in the drug composition in defined ratios. The ratio may provide at least some of the uniqueness of the taggant associated with the drug composition. The taggants, including their relative ratios, may indicate drug composition manufacturer, drug, drug composition, manufacturing batch, dispensing pharmacy, prescribing healthcare provider, healthcare provider's institution, and prescribed user.

The taggants may be detectable in biological samples collected from a user who has consumed the drug composition with the taggants. The biological sample may include urine or feces.

Examples of chemicals which may be used as taggants include polyethylene glycol, copovidone, povidone, propylparaben, methyl paraben, steviol glucuronide, sucralose, oleic acid, trans-anethole, 1, 8-eucalyptol, limonene-2D, riboflavin, and tartaric acid, and salts of tartaric acid.

DETAILED DESCRIPTION OF THE INVENTION

Definitions

Drug, as used herein, means any pharmacologically active agent or mixture of agents.

Biological sample, as used herein, means urine, feces, whole blood, serum, plasma, cerebrospinal fluid, ascites, mucous, gastric gavage, saliva, and breast milk, or any combination thereof.

User, as used herein, means a patient, a participant in a medical study, or any individual who has consumed a drug composition which includes at least one taggant as described herein.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a method of applying taggants to or mixing taggants with drug compositions for later detection of the taggants. The method includes detection of the taggants in a biological sample obtained from the user who has consumed the drug composition and assessment of decay of the drug in the drug composition. In some embodiments, multiple taggants are used. In one embodiment, the first taggant includes multiple chemical molecules in a defined ratio. The ratio may be unique to a variety of details about the drug composition including manufacturer, drug, formulation, drug composition, manufacturing batch, dispensing pharmacy, prescribing healthcare provider, healthcare provider's institution, and prescribed user.

Taggants may be sprayed on pills, included as a powder or liquid ingredient in a pill or capsule or dispersed or dissolved in a liquid medication. The taggants may also be dusted on pills, adhered to pills and pills may be dipped in taggant solutions. In an example the taggants are mixed with the drug in powder form before pill or capsule formation so that the taggants are difficult to separate from the active ingredient in the drug composition. Each taggant may be colorized with a distinct visual color or combination of visual colors corresponding to its respective decay characteristics.

The chemicals included in the taggants may be sensitive to one or more of a variety of conditions. These may include light sensitivity, decay due to temperature sensitivity, and decay due to chemical degradation over time. Decay over time may include oxidation over time which may be a result of oxygen exposure. If the sensitivity to specific conditions and the corresponding decay rate of the taggant is the same or similar to that of the drug in the drug composition, the decay of the drug in the drug composition may be extrapolated to that of the taggants.

In an example, a first chemical is provided in concentration C1 and a second chemical is provided in concentration C2. The first and second chemicals are present in the drug composition in a ratio C2/C1 which represents taggant T21. A third chemical is provided in a concentration of C3 and at a ratio to the second chemical of C3/C1 which represents taggant T31. A user consumes the drug composition with the taggants and the amount of taggants excreted in the user's urine are measured. The reduced amounts of chemicals may be represented by C1*, C2*, and C3* which are present in ratios C1*/C2* and C3*/C1*. The decay characteristics of each of the three chemicals is known and may be extrapolated to indicate the amount of drug in the drug composition that has decayed.

In another example, if the degradation rates of all taggants are different, with enough taggants, paths in a multidimensional space may be used to categorize the drug even in a decayed or partially decayed state. Taggants with different decay rates may reduce the number of possible distinct taggant ratios as one ratio may degrade into a different ratio, so that the second ratio is not useful. However, since the decay ratios describe a bounded trajectory in the multidimensional dimensional space, classification of the taggant aging status is possible based on the position in the multi-dimensional space of concentration ratios.

When a user consumes multiple drug molecules with associated taggants, multivariate techniques may be used to estimate the contributing fractions. Where co-consumption of drugs is indicated, taggant ratios of increased orthogonality may be used to improve multivariate discrimination.

In some embodiments, a plurality of taggants may have negligible or similar decay profiles. An additional taggant may be added that has a different decay profile to assist in extrapolating the decay profile of the taggants to that of the drug in the drug composition.

In some embodiments, the concentration of one or more of the taggants is approximately the same as the concentration of the drug in the drug composition. This scenario assists in providing quantitative information about the amount of drug in the drug composition that enters or leaves the user's body in addition to its decay profile.

In some embodiments, the decay rate of the taggants in response to specific conditions is the approximately the same as the drug in the drug composition. This scenario assists in providing quantitative information about the decay of the drug in the drug composition the user has consumed.

In some embodiments, multiple taggants with different decay sensitivities may be applied to or mixed with the drug composition. For example, one taggant may spontaneously decay over time, one taggant may be sensitive to light exposure, and one taggant may be sensitive to temperatures outside a defined range. When this plurality of taggants is applied to or mixed with a drug composition, the history of the conditions to which the drug composition has been exposed may be determined.

The disclosed method may measure and report or record the detected spectrum or chemical dispersion. A processor may calculate the relative ratios of taggants. Based on the position in a multi-dimensional space of taggant ratios, the amount of decay in one or more axes (for example, age and exposure to heat and light) may be estimated. This calculation may be performed locally on the system or equivalently by a remote processor.

In some embodiments, the disclosed method may function as a drug consumption monitoring system. This system may include a user-identification system for correlating consumed drugs to users. The user-identification system may include methods for identifying users which include bioanalytics (for example, fingerprint, voice print, and electrocardiogram), user registration methods (for example, username and password), behavioral metrics, and combinations thereof.

The biological sample that is analyzed to identify or quantify one or more taggants may include one or more of the following: urine, feces, whole blood, serum, plasma, cerebrospinal fluid, ascites, mucous, gastric gavage, saliva, and breast milk.

In some embodiments, the taggants are detected in the biological sample using one or more of the following analytical techniques: gas chromatography-mass spectrometry, liquid chromatography, capillary zone electrophoresis with UV absorbance, high performance liquid chromatography with UV absorbance, reverse-phase chromatography, fluorescence spectroscopy, high performance thin layer chromatography, UV spectroscopy, infrared spectroscopy, near IR spectroscopy, mid-IR spectroscopy, visible spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, Raman spectroscopy, colorimetric assay, and mass spectrometry. In some embodiments, the taggants are detected in the biological sample using near IR spectroscopy. In some embodiments, the near IR spectroscopy analysis may be conducted using at least one excitation wavelength of between about 1 micron and about 2.5 microns. In some embodiments, spectroscopy analysis may be conducted using at least one excitation wavelength of between about 250 nm and about 800 nm. In some embodiments, the taggants may be measured using colorimetric chemical reactions which may be conducted on a color change chemistry strip.

In some embodiments, the analysis of the taggants may be conducted by an instrument that is within or connected to a medical toilet. The medical toilet may include a urine capture system and a urinalysis system.

The taggants may comprise of one or more of polyethylene glycol, copovidone, povidone, propylparaben, methyl paraben, steviol glucuronide, sucralose, oleic acid, trans-anethole, 1, 8-eucalyptol, limonene-2D, riboflavin, and tartaric acid, and salts of tartaric acid. Trans-anethole is a component of anise oil, 1, 8-eucalyptol is a component of eucalyptus oil, and limonene-2D is a component of orange oil. Consequently, the taggants may include anise oil, eucalyptus oil, and orange oil.

In embodiments in which polyethylene glycol is included in the taggants, the polyethylene glycol may include polymers with an average molecular weight of between about 400 and about 2000. In some embodiments, the polyethylene glycol included in the taggants may include of one or more of the following average molecular weights: 400, 600, 1000, 1500, and 2000. These relatively small average molecular weights are detectable in biological samples, including urine. However, unlike the larger molecular weight polyethylene glycol polymers, they do not act as laxatives.

In some embodiments in which povidone is included in the taggants, the povidone molecules may be polymers that include 25-mers, 30-mers, 90-mers or a combination thereof.

The disclosed method may be used to determine when the user consumed the drug composition. The drug composition may include at least two taggants. The at least two taggants may have known pharmacokinetic properties which may be detectably different from each other. The amount of the taggants measured in a user's bodily waste, particularly over time, may provide an estimate of the time the taggants, and thus the drug, were consumed. In some embodiments, the taggants may be detectable by near infrared spectroscopy. In some embodiments, the taggants may be cleared by the same biological system as the drug in the drug composition. For example, the renal or hepatic systems may clear both the drug and at least one of the taggants. The at least one taggant in the biological sample may, therefore, be used to normalize for impaired liver or kidney function which may impact drug metabolism.

In another example the pharmacokinetic rates of taggant molecules may be different, so the measured ratios of taggants trace a path through a multidimensional taggant ratio space, similar to the case of aging drug compositions, except in this case the ratios are indicative of time since consumption. For instance, the amount of a taggant detected in urine may quickly decrease due to metabolic processing. Urine received soon after consumption may have a higher concentration than urine received a long time after consumption. In contrast, the amount of another taggant measured in the user's urine may decrease more slowly over time. A similar result is achieved for different uptake and elimination rates.

Figure 1A:
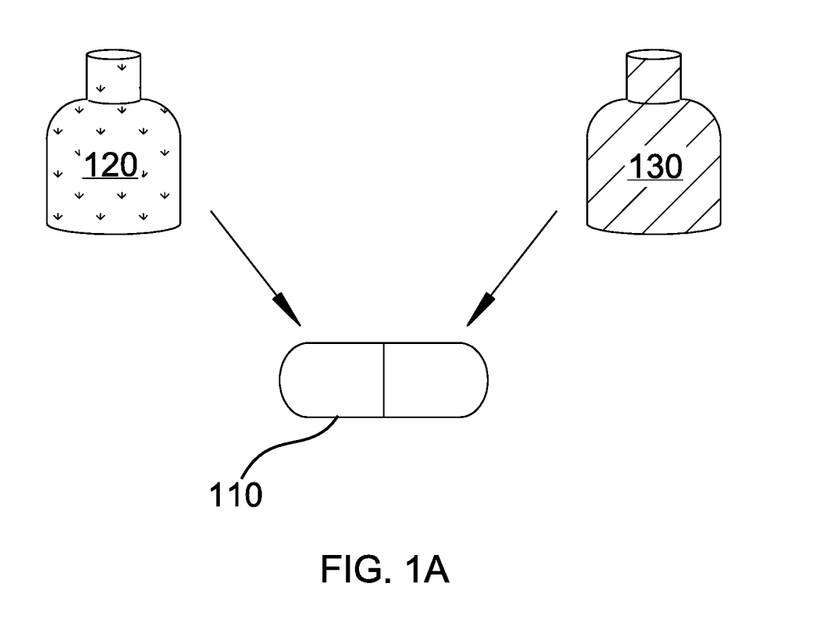
FIG. 1A illustrates two taggants prior to applying to a drug capsule.

Referring now to the drawings, FIG. 1A illustrate drug capsule 110 which includes a drug composition. Drug capsule 110 has not yet been exposed to a taggant. In this embodiment, two chemicals, chemical 120 and chemical 130 are shown and will be sprayed on the surface of a different half of drug capsule 110 according to the arrows.

Figure 1B:
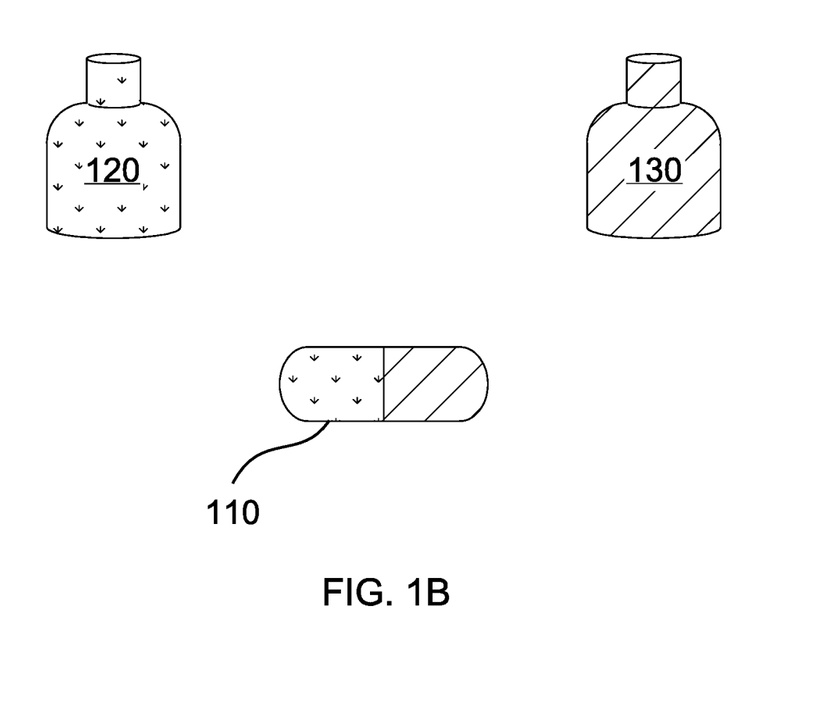
FIG. 1B illustrates the drug capsule of FIG. 1A after the two taggants have been applied.

FIG. 1B shows drug capsule 110 after chemicals 120 and 130 have been sprayed on its surface. The different shadings on drug capsule 110 correlate with the shadings on the bottles of chemicals 120 and 130.

Figure 2:
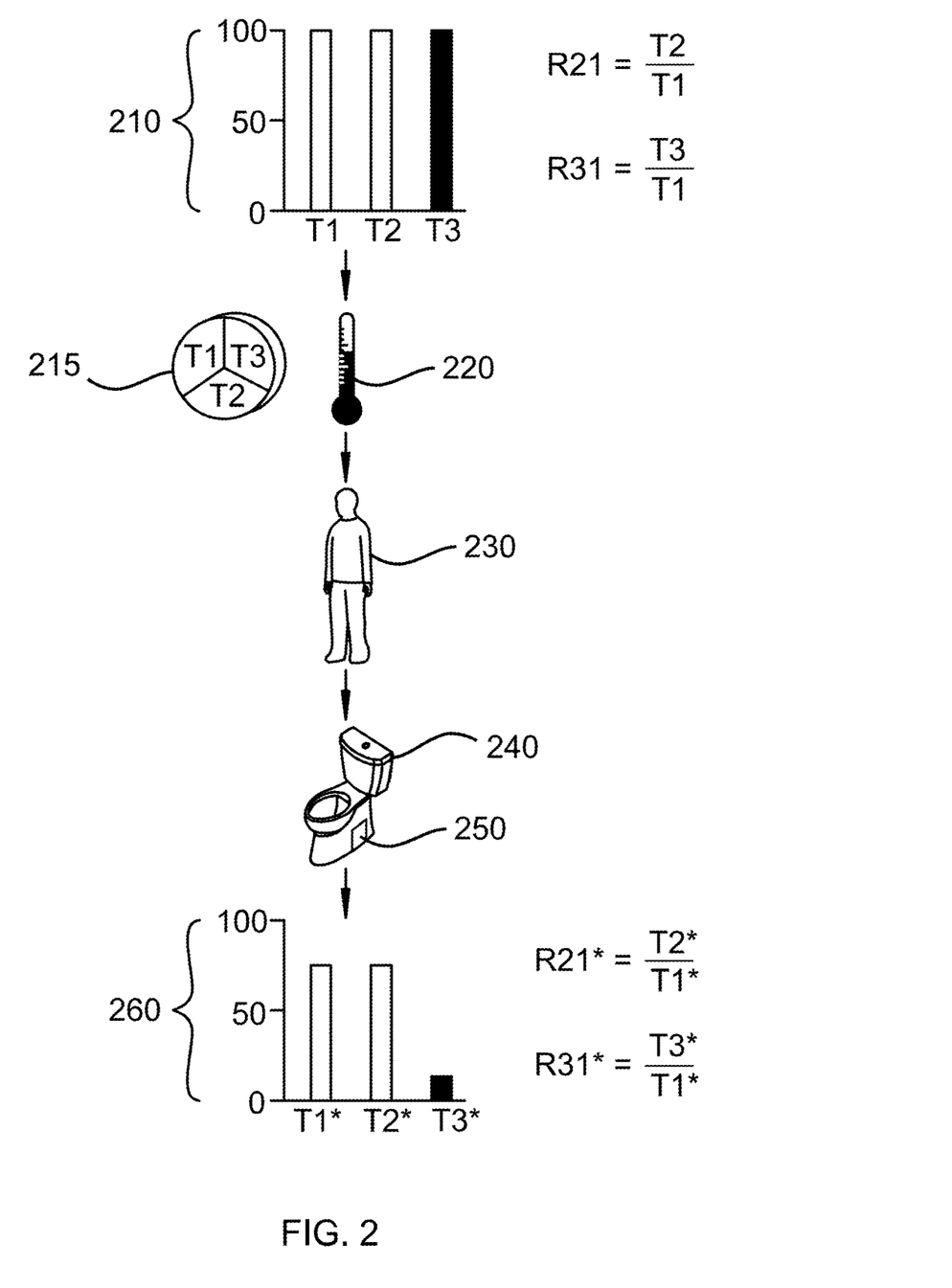
FIG. 2 illustrates a method of using three taggants which have been applied to a medication in defined ratios and consumed by a user to assess drug degradation due to excessive heat.

FIG. 2 illustrates a method of using three chemicals as taggants for a drug composition. The three chemicals are T1, T2, and T3 and their original amounts are shown as 100% in bar graph 210. To the right of bar graph 210, the original ratios of chemicals T1, T2, and T3 are shown. The first ratio, R21, is the ratio of T2 to T1. The second ratio, R31, is the ratio of T3 to T1. R21 and R31 represent two taggants. They are unique to other taggants because of the chemicals and because of their relative ratios. The three chemicals have been applied to a drug composition, illustrated as tablet 215 in ratios R21 and R31. At some point, tablet 215 is exposed to temperature 220, illustrated in FIG. 2 as a thermometer. Temperature 220 is above the recommended storage temperature for tablet 215 because the drug in tablet 215 is heat sensitive. Consequently, at least one chemical which is similarly heat sensitive is included in the taggants. T3 is especially heat sensitive so failure to detect the original amount of T3 in a user's biological waste indicates heat exposure.

User 230 consumes tablet 215 and then urinates in medical toilet 240. Medical toilet 240 includes spectrophotometer 250 which analyses the urine from user 230 using wavelengths in the near IR range. The percentages of the original amounts of T1, T2, and T3 that were applied to tablet 215 at the time of manufacture are measured in the near IR spectroscopy analysis and are found to be reduced. The altered T1, T2, and T3 are presented in bar graph 260 as T1*, T2*, and T3* respectively. The original ratios R21 and R31 are also altered and presented at R21* and R31* respectively. This analysis indicates that the drug in tablet 215 has been exposed to excessive heat and tablet 215 may have contained less active drug at the time user 230 consumed than it did at the time of manufacture.

Figure 3:
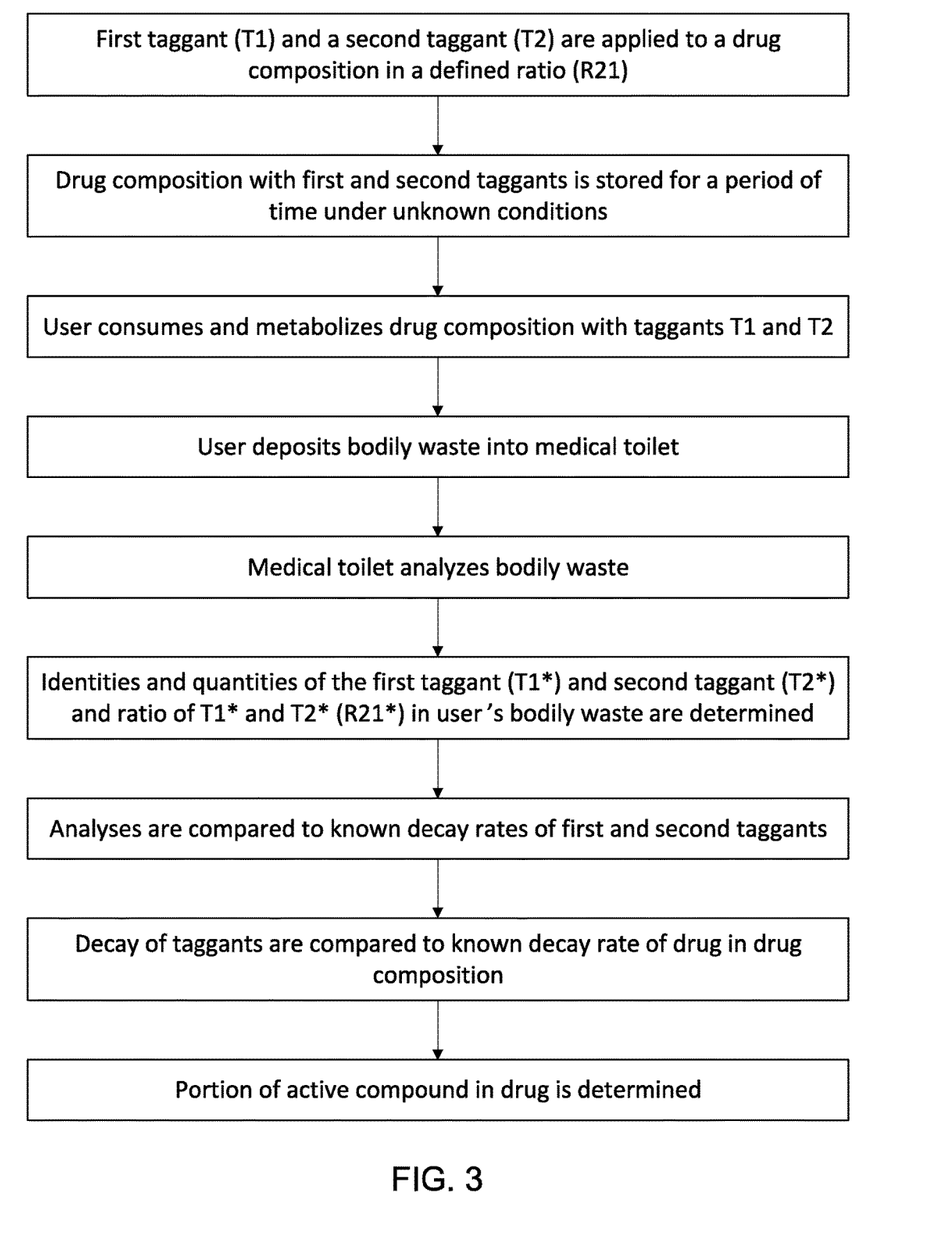
FIG. 3 provides a flow chart which includes steps which may be used in performing an embodiment of a method of using the disclosed drug tagging system to assess drug degradation over time.

FIG. 3 is a flow chart illustrating a series of steps which may be performed to assess the length of time a drug has been stored prior to consumption. In this embodiment, there are two taggants, T1 and T2 which have been applied to a drug composition in defined ratio R21. The drug composition with the two taggants is stored for a period of time under unknown conditions. The drug composition has a shelf life beyond which the drug becomes less active. The drug may also be sensitive to other conditions, for example, light and extreme temperature. A user consumes the drug composition along with the two taggants then deposits bodily waste into a medical toilet. The medical toilet includes a spectrometer which analyzes the bodily waste using near IR spectroscopy.

Figure 4:
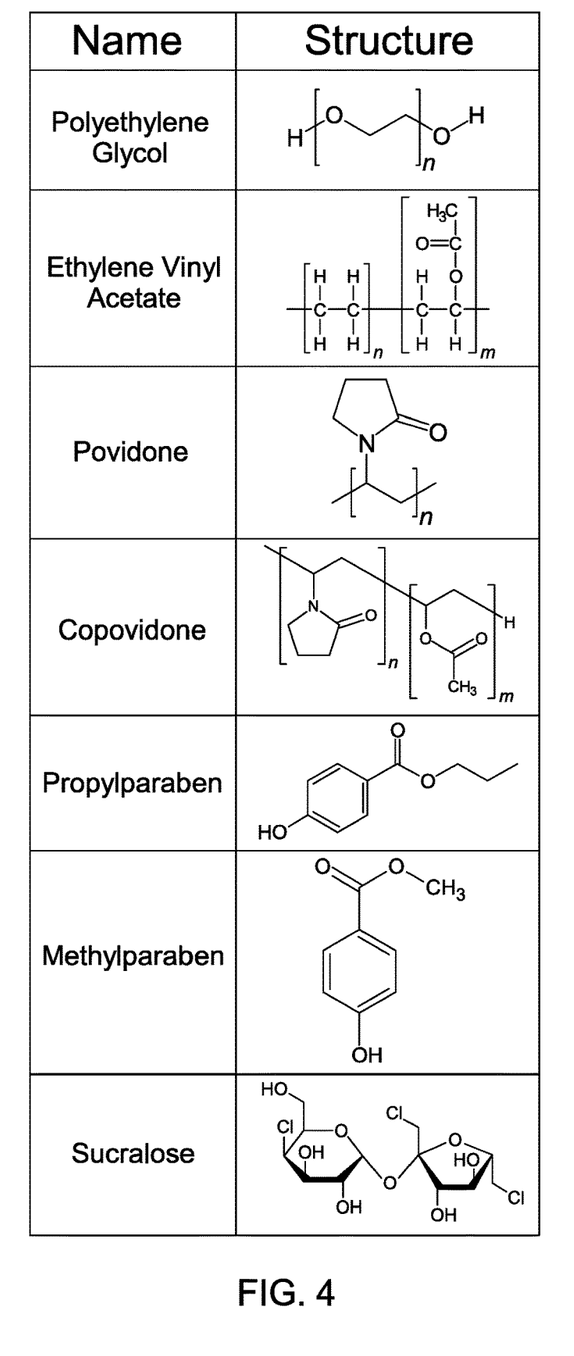
FIG. 4 is a table showing the names and chemical structures of examples of relatively stable molecules which may be used in taggants according to the disclosure.

The near IR spectroscopy analysis identifies and quantifies the two taggants. The amount of the taggants identified in the bodily waste is reduced relative to the amount applied to the drug composition. The reduced amounts of T1 and T2 are referred to as T1* and T2* and have been found in the bodily waste in altered ratio R21*. The decays of the two taggants are compared to known decay rate of the drug in the drug composition in response to different environmental and temporal conditions. The portion of active drug in the drug composition at the time the user consumed the drug composition is then determined FIG. 4 provides a table which lists examples of chemical entities which may be used in taggants according to the disclosure along with their chemical structures. These include polyethylene glycol, ethylene-vinyl acetate, copovidone, povidone, propylparaben, sucralose, and methyl paraben. The compounds in the table of FIG. 1 are relatively stable over time.

Figure 5:
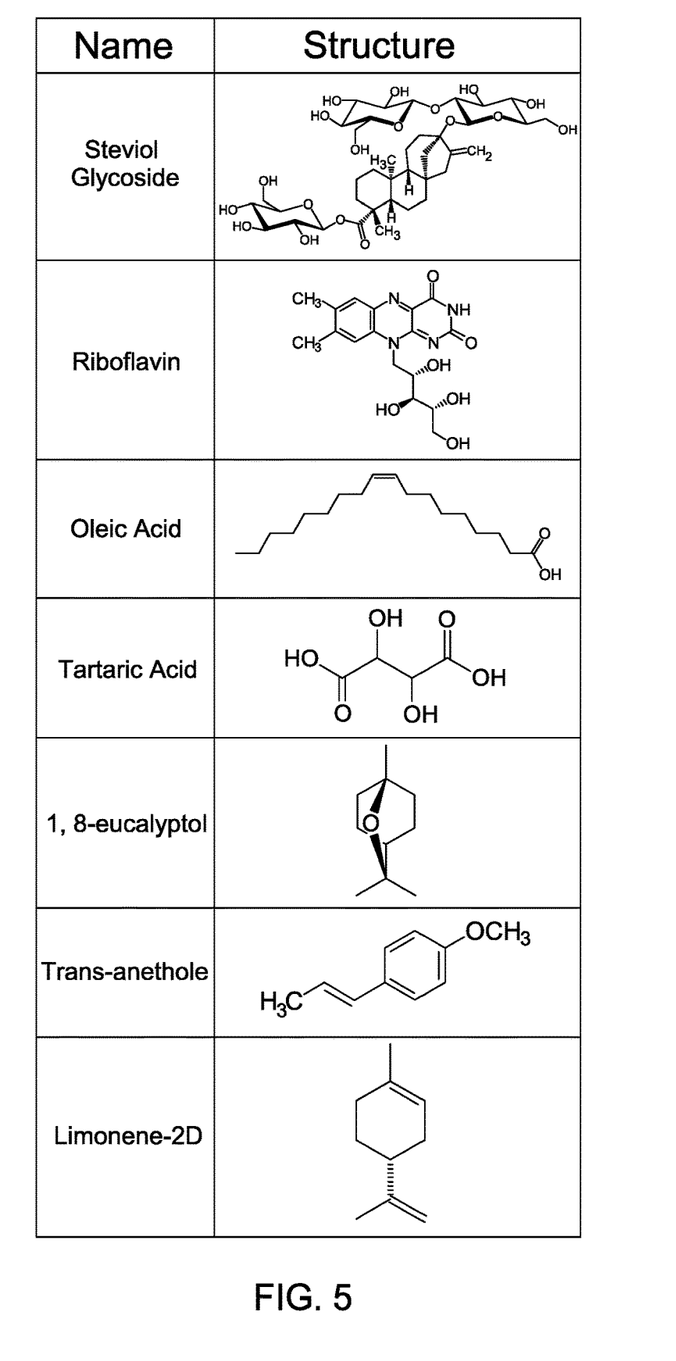
FIG. 5 is a table showing the names and chemical structures of examples of partially metabolized or degraded molecules which may be used in taggants according to the disclosure.

FIG. 5 provides a table which lists examples of chemical entities which may be used in taggants according to the disclosure along with their chemical structures. These include steviol glucuronide, sucralose, oleic acid, trans-anethole, 1, 8-eucalyptol, limonene-2D, riboflavin, and tartaric acid, and salts of tartaric acid. Trans-anethole is a component of anise oil, 1, 8-eucalyptol is a component of eucalyptus oil, and limonene-2D is a component of orange oil. Accordingly, anise oil, eucalyptus oil, and orange oil may be used in taggants. These chemical entities are relatively unstable over time so may be used to assess the amount of time that has passed after applying the tag to the drug composition or nutritional composition.

Figure 6:
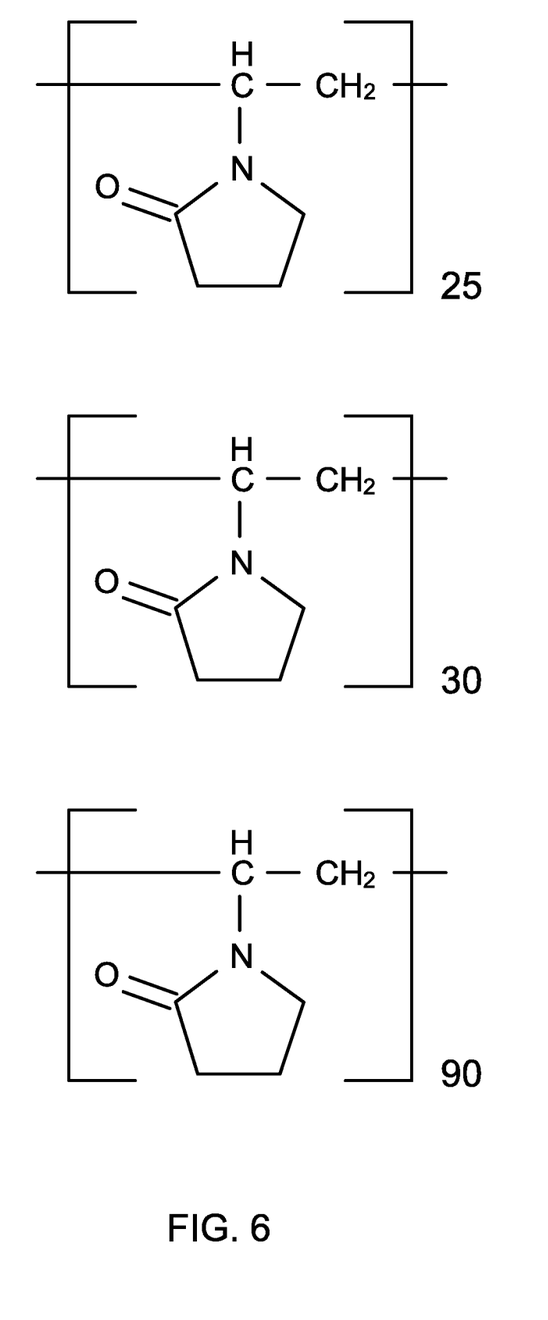
FIG. 6 shows three variations of povidone which may be used in taggants according to the disclosure.

FIG. 6 shows three forms of povidone which may be used in taggants according to the disclosure. These include polymers of varying sizes including a 25-mer, a 30-mer, and a 90-mer.

Figure 7:
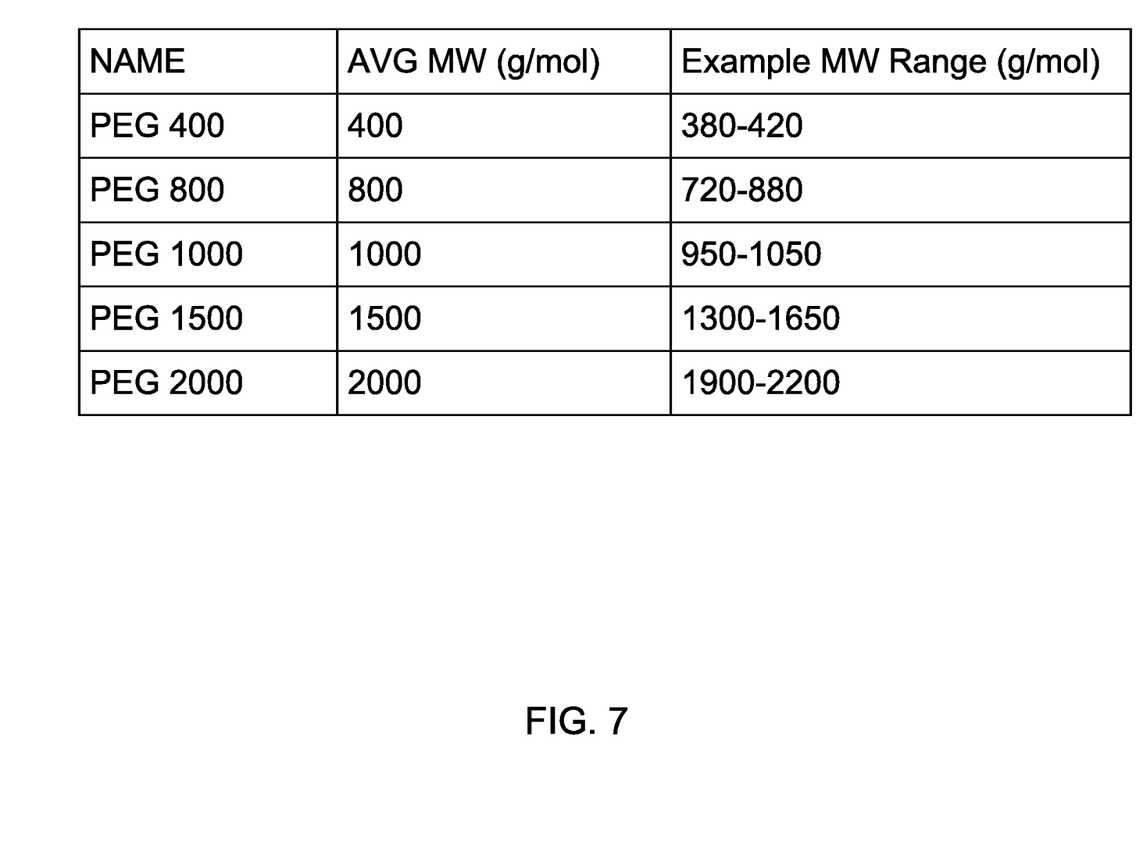
FIG. 7 is a table showing variations of PEGs which may be used in taggants according to the disclosure.

FIG. 7 provides a table which lists examples of polyethylene glycols of varying average molecular weights. These include PEG 400, PEG 800, PEG 1000, PEG 1500, and PEG 2000. Polyethylene glycol is a polymer made of varying numbers of monomers and each polyethylene glycol solution may be comprised of a range of molecular weights, depending on the number of monomers in the polymers, with an average molecular weight.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of tagging a drug composition to detect decay of an active ingredient in the drug composition comprising the steps of:
   a. providing a drug composition, the drug composition comprising a drug;
   b. providing a first taggant, wherein the first taggant is photosensitive;
   c. providing a second taggant, wherein the second taggant is heat sensitive and resistant to light; and
   d. adding the first taggant and the second taggant to the drug composition, wherein both the first taggant and the second taggant are detectable in a biological sample after consumption; and wherein the first taggant and the second taggant are independently selected from the following: polyethylene glycol, copovidone, povidone, propylparaben, methyl paraben, steviol glucuronide, sucralose, oleic acid, trans-anethole, 1,8-eucalyptol, limonene-2D, riboflavin, and tartaric acid, and salts of tartaric acid.

2. The method of claim 1, wherein the first taggant and the second taggant are added in a defined ratio.

3. The method of claim 2, wherein the defined ratio is indicative of one of the following: drug composition manufacturer, drug, drug composition, manufacturing batch, dispensing pharmacy, prescribing healthcare provider, healthcare provider's institution, and prescribed user.

4. The method of claim 1, wherein either the first taggant, the second taggant, or both the first and second taggant consist of polyethylene glycol, and wherein the polyethylene glycol comprises polymers of one or more of the following average molecular weights: 400, 600, 1000, 1500, and 2000.

5. The method of claim 1, wherein either the first taggant, the second taggant, or both the first and second taggant consist of polyethylene glycol, and wherein the polyethylene glycol comprises polymers with an average molecular weight of between about 400 and about 2000.

6. The method of claim 1, wherein either the first taggant, the second taggant, or both the first and second taggant consists of povidone molecules, and wherein the povidone molecules consist of one or more of the following number of monomers: 25, 30, and 90.

7. The method of claim 1, wherein the biological sample comprises one or more of the following: urine, feces, whole blood, serum, plasma, cerebrospinal fluid, ascites, mucous, gastric gavage, saliva, and breast milk.

8. The method of claim 1, wherein the first taggant and the second taggant are detectable in the biological sample using one or more of the following analytical techniques: gas chromatography-mass spectrometry, liquid chromatography, capillary zone electrophoresis with UV absorbance, high performance liquid chromatography with UV absorbance, reverse-phase chromatography, fluorescence spectroscopy, high performance thin layer chromatography, UV spectroscopy, infrared spectroscopy, near IR spectroscopy, mid-IR spectroscopy, visible spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, Raman spectroscopy, colorimetric assay, and mass spectrometry.

9. The method of claim 8, wherein the analytical technique is performed by an instrument connected to a medical toilet.

10. The method of claim 1, wherein at least one of the first taggant and the second taggant are detectable using a near IR absorption spectroscopy technique and at least one excitation wavelength of between about 1 micron and about 2.5 microns.

11. The method of claim 1, wherein at least one of the first taggant and the second taggant are detectable using an absorption spectroscopy technique and at least one excitation wavelength of between about 250 nm and about 800 nm.

12. The method of claim 1, wherein the first taggant has a first decay characteristic and the second taggant has a second decay characteristic which are independently selected from the following: decay due to light sensitivity, decay due to temperature sensitivity, and decay due to chemical degradation over time.

13. The method of claim 1, wherein a concentration of the first taggant, a concentration of the second taggant, or the concentration of both the first and the second taggant is approximately the same as a concentration of the drug.

14. The method of claim 12, wherein the first decay characteristic, the second decay characteristic, or both the first and the second decay characteristics are approximately the same as a decay characteristic of the drug.

15. The method of claim 14, which further includes a third taggant, wherein the third taggant is stable in response to light, extreme temperature, oxygen exposure, and time relative to the first and second taggants.

16. The method of claim 15, wherein the third taggant is cleared by the same biological system as the drug.

17. The method of claim 15, providing each of the first taggant, second taggant, and third taggant with a distinct visual color or combination of visual colors corresponding to their respective decay characteristics.

* * * * *